US010471132B2

(12) United States Patent
Mingozzi et al.

(10) Patent No.: US 10,471,132 B2
(45) Date of Patent: Nov. 12, 2019

(54) TREATMENT OF HYPERBILIRUBINEMIA

(71) Applicants: GENETHON, Evry (FR); INTERNATIONAL CENTRE FOR GENETIC ENGINEERING AND BIOTECHNOLOGY, Trieste (IT)

(72) Inventors: Federico Mingozzi, Paris (FR); Giuseppe Ronzitti, Paris (FR); Fanny Collaud, Paris (FR); Andrés Muro, Trieste (IT); Giulia Bortolussi, Travesio (IT)

(73) Assignees: GENETHON, Evry (FR); INTERNATIONAL CENTRE FOR GENETIC ENGINEERING AND BIOTECHNOLOGY, Trieste (IT)

( * ) Notice: Subject to any disclaimer, the term of this patent is extended or adjusted under 35 U.S.C. 154(b) by 0 days.

(21) Appl. No.: 15/303,834

(22) PCT Filed: Apr. 27, 2015

(86) PCT No.: PCT/EP2015/059099
§ 371 (c)(1),
(2) Date: Oct. 13, 2016

(87) PCT Pub. No.: WO2015/162302
PCT Pub. Date: Oct. 29, 2015

(65) Prior Publication Data
US 2017/0028036 A1 Feb. 2, 2017

(30) Foreign Application Priority Data

Apr. 25, 2014 (EP) .................................... 14305622
Dec. 4, 2014 (EP) .................................... 14196400

(51) Int. Cl.
*A61K 38/45* (2006.01)
*C12N 15/86* (2006.01)
*A61K 48/00* (2006.01)
*C12N 9/10* (2006.01)
*C12N 7/00* (2006.01)

(52) U.S. Cl.
CPC .......... *A61K 38/45* (2013.01); *A61K 48/0058* (2013.01); *A61K 48/0066* (2013.01); *C12N 7/00* (2013.01); *C12N 9/1051* (2013.01); *C12N 15/86* (2013.01); *C12Y 204/01017* (2013.01); *C12N 2750/14143* (2013.01); *C12N 2830/008* (2013.01); *C12N 2830/42* (2013.01)

(58) Field of Classification Search
CPC ................ A61K 38/45; A61K 48/0058; A61K 48/0066; C12Y 204/01017
See application file for complete search history.

(56) References Cited

FOREIGN PATENT DOCUMENTS

| WO | WO 97/21825 | 6/1997 | |
|---|---|---|---|
| WO | WO-9721825 A1 * | 6/1997 | ............. C12N 15/86 |
| WO | WO 2006/119137 | 11/2006 | |
| WO | WO 2007/120533 | 10/2007 | |
| WO | WO-2007120533 A2 * | 10/2007 | ......... A61K 48/0058 |
| WO | WO 2011/106759 | 9/2011 | |
| WO | WO 2013/063383 | 5/2013 | |
| WO | WO-2013063383 A2 * | 5/2013 | ........... C12N 9/0051 |
| WO | WO 2013/151666 | 10/2013 | |
| WO | WO-2013151666 A2 * | 10/2013 | ......... A61K 48/0066 |

OTHER PUBLICATIONS

Fath et al PLOS One, 6, e17596 (Year: 2011).*
Pastore et al Molecular Therapy vol. 21, Supplement 1, S192-S193, (Year: 2013).*
Seppen et al Molecular Therapy, 13, 1085-1092 (Year: 2006).*
Wu et al Molecular Therapy, 16, 280-289 (Year: 2008).*
Stephan et al Plos ONE, e17596, (Year: 2011).*
Son et al Journal of Biological Chemistry, 18037-18044 (Year: 2003).*
Kamhi et al Nucleic acid Res. 2006, 3421-3433.*
Fath, S. et al. "Multiparameter RNA and Codon Optimization: A Standardized Tool to Assess and Enhance Autologous Mammalian Gene Expression" *PLoS One*, Mar. 3, 2011, pp. 1-14, vol. 6, Issue 3, e17596.
Kamhi, E. et al. "AUG sequences are required to sustain nonsense-codon-mediated suppression of splicing" *Nucleic Acids Research*, Jul. 19, 2006, pp. 3421-3433, vol. 34, No. 12.
Kozak, M. "Some Thoughts About Translational Regulation: Forward and Backward Glances" *Journal of Cellular Biochemistry*, 2007, pp. 280-290, vol. 102.
Okayama, H. et al. "A cDNA Cloning Vector That Permits Expression of cDNA Inserts in Mammalian Cells" *Molecular and Cellular Biology*, Feb. 1983, pp. 280-289, vol. 3, No. 2.
Pastore, N. et al. "Development of AAV2/8-Mediated Gene Therapy Clinical Trial for Crigler-Najjar Syndrome Type I: Optimization of Liver-Specific Expression Cassette" *Molecular Therapy*, May 2013, #499, pp. S192-S193, vol. 21, Supp. 1.
Seppen, J. et al. "Adeno-associated Virus Vector Serotypes Mediate Sustained Correction of Bilirubin UDP Glucuronosyltransferase Deficiency in Rats" *Molecular Therapy*, Jun. 2006, pp. 1085-1092, vol. 13, No. 6.
Son, G.H. et al. "Excision of the First Intron from the Gonadotropin-releasing Hormone (GnRH) Transcript Serves as a Key Regulatory Step for GnRH Biosynthesis" *The Journal of Biological Chemistry*, May 16, 2003, pp. 18037-18044, vol. 278, No. 2.
Wu, Z. et al. "Optimization of Self-complementary AAV Vectors for Liver-directed Expression Results in Sustained Correction of Hemophilia B at Low Vector Dose" *Molecular Therapy*, Feb. 2008, pp. 280-289, vol. 16, No. 2.

(Continued)

*Primary Examiner* — Anoop K Singh
(74) *Attorney, Agent, or Firm* — Saliwanchik, Lloyd & Eisenschenk

(57) ABSTRACT

The invention relates to a nucleic acid sequence useful in the treatment of hyperbilirubinemia, in particular in the treatment of Crigler-Najjar syndrome. More particularly, the nucleic acid sequence of the present invention is a codon-optimized UGT1A1 coding sequence.

19 Claims, 7 Drawing Sheets
Specification includes a Sequence Listing.

(56) References Cited

OTHER PUBLICATIONS

Database EBI [Online] Accession No. BC128414, "*Homo sapiens* UDP glucuronosyltransferase 1 family, polypeptide A1, mRNA" Dec. 7, 2006, pp. 1-4, XP-002729220.
Written Opinion in International Application No. PCT/EP2015/059099, dated Nov. 11, 2015, pp. 1-12.

\* cited by examiner

A. AAV8-hAAT-wtUGT1A1

B. AAV8-hAAT-coUGT1A1v2.1

TREATMENT OF HYPERBILIRUBINEMIA

CROSS-REFERENCE TO RELATED APPLICATION

This application is the U.S. national stage application of International Patent Application No. PCT/EP2015/059099, filed Apr. 27, 2015.

The Sequence Listing for this application is labeled "Seq-List.txt" which was created on Sep. 5, 2016 and is 16 KB. The entire content of the sequence listing is incorporated herein by reference in its entirety.

FIELD OF THE INVENTION

The invention relates to a nucleic acid sequence useful in the treatment of hyperbilirubinemia, in particular in the treatment of Crigler-Najjar syndrome. More particularly, the nucleic acid sequence of the present invention is a codon-optimized human UGT1A1 coding sequence.

BACKGROUND OF THE INVENTION

Crigler-Najjar syndrome (CN) is an autosomal recessive disorder with severe unconjugated hyperbilirubinemia due to deficiency of bilirubin UDP-glucuronosyltransferase isozyme 1A1 (UGT1A1) encoded by the UGT1A1 gene (OMIM #218800). The prevalence of CN is about 1/1000000 individuals at birth, making CN an ultra-rare disease. Current therapy for CN relies on phototherapy to prevent elevations of serum bilirubin levels. For the mild form of the disease, also known as CN type II, phenobarbital can be used to lower bilirubinemia.

Nonetheless patients are potentially exposed to the risk of life-threatening spikes in bilirubin in blood and liver transplantation remains the only curative treatment. In its most severe form, the disease is lethal due to bilirubin-induced neurological damage unless phototherapy is applied from birth. Despite the availability of a therapy, CN remains an unmet medical need for a number of reasons including loss of efficacy of phototherapy during growth, poor compliance due to the limitation of phototherapy itself (which needs to be carried on for 10-12 hours each day), and occurrence of pathological liver changes over time, which may require liver transplantation.

Different animal models of the disease exist, including the naturally occurring Gunn rat and a more recent knock-in mouse model of the disease, developed by Dr. Muro at ICGEB in Trieste, Italy, which carries the same mutation present in the Gunn rat (Bortolussi et al., 2012). Gunn rats present high bilirubin levels in serum and they have cerebellar hyploplasia; CN mice have a much more severe phenotype, and die soon after birth if not promptly treated with phototherapy or gene therapy (Bortolussi et al., 2012).

Prior studies aimed at developing a gene-based therapy for CN showed that therapeutic efficacy could be achieved using AAV vectors delivered to the liver (Bortolussi et al., 2012; Seppen et al., 2006). However, a need for a more efficient therapeutic strategy still exists.

Gilbert's syndrome (or GS; OMIM #218800) is a genetic liver disorder and the most common hereditary cause of increased bilirubin. It is found in up to 3-12% of the population. GS is also caused by mutations in the UGT1A1 gene. Therapeutic strategies aiming at reducing hyperbilirubinemia would therefore also be advantageously implemented in the treatment of GS.

SUMMARY OF THE INVENTION

The present invention relates to a codon optimized UGT1A1 coding sequence derived from the human UGT1A1 cDNA. More particularly, the codon optimized UGT1A1 coding sequence has an increased GC content and/or has a decreased number of alternative open reading frames as compared to the wild-type human coding sequence of SEQ ID NO:1. For example, nucleic acid sequence of the invention results in an at least 2, 3, 4, 5 or 10% increase of GC content of the UGT1A1 sequence as compared to the sequence of the wild-type human UGT1A1 sequence. In a particular embodiment, the nucleic acid sequence of the invention results in a 2, 3, 4 or, more preferably, 5% or 10% (preferably 5%) increase of GC content of the UGT1A1 sequence as compared to the sequence of the wild-type human UGT1A1 sequence. In a particular embodiment, the nucleic acid sequence of the invention encoding a codon optimized human UGT1A1 protein is "substantially identical", that is, about 70% identical, more preferably about 80% identical, even more preferably about 90% identical, even more preferably about 95% identical, even more preferably about 97%, 98% or even 99% identical to SEQ ID NO: 2 or SEQ ID NO: 3. In a particular embodiment, the invention relates to a nucleic acid sequence encoding a codon optimized human UGT1A1 protein, wherein the nucleic acid sequence comprises the sequence shown in SEQ ID NO: 2 or SEQ ID NO:3.

Advantageously, the codon optimized nucleic acid of the invention provides for improved reduction in bilirubin levels and/or for decreased immunogenicity.

The invention also relates to a nucleic acid construct comprising a nucleic acid sequence of the invention. The nucleic acid construct may correspond to an expression cassette comprising the nucleic acid sequence of the invention, operably linked to one or more expression control sequences or other sequences improving the expression of a transgene. Such sequences are known in the art, such as promoters, enhancers, introns, polyA signals, etc. In particular, the expression cassette may include a promoter. The promoter may be an ubiquitous or tissue-specific promoter, in particular a liver specific promoter. More particularly the promoter is a liver-specific promoter such as the alpha-1 antitrypsin promoter (hAAT) (SEQ ID NO:4), the transthyretin promoter, the albumin promoter, the thyroxine-binding globulin (TBG) promoter, etc. Other useful liver-specific promoters are known in the art, for example those listed in the the Liver Specific Gene Promoter Database compiled by the Cold Spring Harbor Laboratory (http://rulai.cshl.edu/LSPD/). Representative ubiquitous promoters include the cytomegalovirus enhancer/chicken beta actin (CAG) promoter, the cytomegalovirus enhancer/promoter (CMV), the PGK promoter, the SV40 early promoter, etc. In a particular embodiment, the promoter is associated with an enhancer sequence such as the ApoE control region, such as the human ApoE control region (or Human apolipoprotein E/C-I gene locus, hepatic control region HCR-1—Genbank accession No. U32510, shown in SEQ ID NO:11). In a particular embodiment, an enhancer sequence such as the ApoE sequence is associated with a liver-specific promoter such as those listed above, and in particular such as the hAAT promoter.

In a particular embodiment, the nucleic acid construct comprises an intron, in particular an intron placed between the promoter and the coding sequence. An intron may be introduced to increase mRNA stability and the production of the protein. In a particular embodiment, the nucleic acid construct comprises a human beta globin b2 (or HBB2) intron, a coagulation factor IX (FIX) intron, an SV40 intron or a chicken beta-globin intron. In a particular embodiment, the nucleic acid construct of the invention contains a modified intron (in particular a modified HBB2 or FIX intron) designed to decrease the number of, or even totally remove, alternative open reading frames (ARFs) found in said intron. Preferably, ARFs are removed whose length spans over 50 bp and have a stop codon in frame with a start codon. ARFs may be removed by modifying the sequence of the intron. For example, modification may be carried out by way of nucleotide substitution, insertion or deletion, preferably by nucleotide substitution. As an illustration, one or more nucleotides, in particular one nucleotide, in an ATG or GTG start codon present in the sequence of the intron of interest may be replaced resulting in a non-start codon. For example, an ATG or a GTG may be replaced by a CTG, which is not a start codon, within the sequence of the intron of interest.

The classical HBB2 intron used in nucleic acid constructs is shown in SEQ ID NO:5. For example, this HBB2 intron may be modified by eliminating start codons (ATG and GTG codons) within said intron. In a particular embodiment, the modified HBB2 intron comprised in the construct has the sequence shown in SEQ ID NO:6. The classical FIX intron used in nucleic acid constructs is derived from the first intron of human FIX and is shown in SEQ ID NO:7. FIX intron may be modified by eliminating start codons (ATG and GTG codons) within said intron. In a particular embodiment, the modified FIX intron comprised in the construct of the invention has the sequence shown in SEQ ID NO:8. The classical chicken beta-globin intron used in nucleic acid constructs is shown in SEQ ID NO:9. Chicken beta-globin intron may be modified by eliminating start codons (ATG and GTG codons) within said intron. In a particular embodiment, the modified chicken beta-globin intron comprised in the construct of the invention has the sequence shown in SEQ ID NO:10.

The inventors have shown that such a modified intron, in particular a modified HBB2 or FIX intron, has advantageous properties and can significantly improve the expression of the transgene. Furthermore, by decreasing the number of ARFs within the intron included within the construct of the invention, it is believed that the construct immunogenicity is also decreased.

The invention thus also relates to an intron intended to be used in an expression cassette, and which is modified to increase the efficiency of the expression of a transgene placed in the cassette. In particular, the invention relates to a modified intron derived from a known intron, but where the number of ARFs has been decreased, or where ARFs have been totally removed. In a particular embodiment, the invention relates to a modified HBB2 intron with a decreased number of ARFs, or with no ARFs. In a further particular embodiment, the modified HBB2 intron is the one shown in SEQ ID NO:6. In another embodiment, the invention relates to a modified FIX intron with a decreased number of ARFs, or with no ARFs. In a further particular embodiment, the modified FIX intron is the one shown in SEQ ID NO:8. In another embodiment, the invention relates to a modified chicken beta-globin intron with a decreased number of ARFs, or with no ARFs. In a further particular embodiment, the modified chicken beta-globin intron is the one shown in SEQ ID NO:10. A further aspect of the invention relates to a nucleic acid construct, a vector such as a viral vector, in particular an AAV vector, and a cell comprising the modified intron of the invention. The nucleic acid construct may include additional expression control sequences such as a promoter and/or an enhancer, such as those described herein and others. The modified intron as disclosed herein increases the efficiency of expression of a transgene placed in the nucleic acid construct, such as a gene of interest like a therapeutic gene. In the context of the this aspect of the invention, a "therapeutic gene" generally refers to a gene encoding a therapeutic protein which is useful in the treatment of a pathological condition. The therapeutic gene, when expressed, confers a beneficial effect on the cell or tissue in which it is present, or on a patient in which the gene is expressed. Examples of beneficial effects include amelioration of a sign or symptom of a condition or disease, prevention or inhibition of a condition or disease, or conferral of a desired characteristic. Therapeutic genes include genes that partially or wholly correct a genetic deficiency in the patient. In particular, the therapeutic gene may be, without limitation, a nucleic acid sequence encoding a protein useful in gene therapy to relieve deficiencies caused by missing, defective or sub-optimal levels of said protein in a cell or tissue of a subject. Therefore, the present invention relates to a nucleic acid construct, a vector such as a viral vector, in particular an AAV vector, and a cell comprising the modified intron of the invention, and further comprising a therapeutic gene of interest, for use in gene therapy. The present invention may generally be applied for therapy of any disease that may be treated by expression of a therapeutic gene in a cell or tissue of a subject. These include, for example, proliferative diseases (cancers, tumors, dysplasias, etc.); infectious diseases; viral diseases (induced, e.g., by the Hepatitis B or C viruses, HIV, herpes, retroviruses, etc.); genetic diseases (cystic fibrosis, dystroglycanopathies, myopathies such as Duchenne Muscular Myopathy; myotubular myopathy; hemophilias; sickle-cell anemia, sickle cell disease, Fanconi's anemia; diabetes; amyotrophic lateral sclerosis, mononeurones diseases such as spinal muscular atrophy, spinobulbar muscular atrophy, or Charcot-Marie-Tooth disease; arthritis; severe combined immunodeficiencies (such as RS-SCID, ADA-SCID or X-SCID), Wiskott-Aldrich syndrome, X-linked thrombocytopenia, congenital neutropenia, Chronic granulomatous disease, etc.); cardiovascular diseases (restenosis, ischemia, dyslipidemia, homozygous familial hypercholesterolemia, etc.); neurological diseases (psychiatric diseases, neurodegenerative diseases such as Parkinson's or Alzheimer's, Huntington's disease addictions (e.g., to tobacco, alcohol, or drugs), epilepsy, Canavan's disease, adrenoleukodystrophy, etc.); eye diseases such as retinitis pigmentosa, Leber congenital amaurosis, Leber hereditary optic neuropathy, Stargardt disease; lysosomal storage diseases such as San Filippo syndrome; and hyperbilirubinemia such as CN type I or II or Gilbert's syndrome, Pompe disease, etc. As mentioned above, and further developed in the following disclosure, to effect expression of a transgene such as a therapeutic gene in a recipient host cell, it is preferably operably linked to a promoter, either its own or a heterologous promoter. A large number of suitable promoters are known in the art, the choice of which depends on the desired level of expression of the product encoded by the therapeutic gene; whether one wants constitutive expression, cell-specific or tissue-specific expression, etc. The nucleic acid construct comprising the modified intron, the vector comprising said nucleic acid construct or the cell comprising said construct or said vector may further be used in gene or cell therapy when the gene of interest is a therapeutic gene as defined above.

In a particular embodiment, the nucleic acid construct of the invention is an expression cassette comprising, in the 5' to 3' orientation, a promoter optionally preceded by an enhancer, the codon-optimized UGT1A1 coding sequence of the invention, and a poly adenylation signal. In a particular embodiment, the nucleic acid construct of the invention is an expression cassette comprising, in the 5' to 3' orientation, a promoter optionally preceded by an enhancer, (such as the ApoE control region), an intron (in particular an intron as defined above), the codon-optimized UGT1A1 coding sequence of the invention, and a poly adenylation signal. In a further particular embodiment, the nucleic acid construct of the invention is an expression cassette comprising, in the 5' to 3' orientation, an enhancer such as the ApoE control region, a promoter, an intron (in particular an intron as defined above), the codon-optimized UGT1A1 coding sequence of the invention, and a poly adenylation signal.

The invention also relates to a vector comprising a nucleic acid sequence as disclosed herein. In particular, the vector of the invention is a vector suitable for use in gene therapy. For example, the vector may be a plasmid vector. More particularly, the vector is a viral vector suitable for gene therapy targeting liver tissue or cells. In this case, the nucleic acid construct of the invention also contains sequences suitable for producing an efficient viral vector, as is well known in the art. In a further particular embodiment, the viral vector is an AAV vector, such as an AAV vector suitable for transducting liver tissues or cells, more particularly an AAV-1, -2, -5, -6, -7, -8, -9, -rh10, -rh74, -dj, etc., vector or a retroviral vector such as a lentiviral vector. In a further embodiment, the AAV vector comprises a genome which is either single stranded or self-complementary double stranded. Preferably for the practice of the present invention, the AAV genome is single stranded. As is known in the art, depending on the specific viral vector considered for use, suitable sequences will be introduced in the nucleic acid construct of the invention for obtaining a functional viral vector. Suitable sequences include AAV ITRs for an AAV vector, or LTRs for lentiviral vectors. As such, the invention also relates to an expression cassette as described above, flanked by an ITR or an LTR on each side.

In a particularly preferred embodiment, the invention relates to an AAV vector comprising, in a single-stranded or double-stranded, self-complementary genome (e.g. a single-stranded genome), the nucleic acid construct of the invention. In a particular embodiment, the nucleic acid construct comprises the sequence shown in SEQ ID NO:2 or SEQ ID NO:3. In one embodiment, the AAV vector is an AAV8 vector. In a further particular embodiment, said nucleic acid is operably linked to a promoter, especially an ubiquitous or liver-specific promoter. According to a specific variant embodiment, the promoter is an ubiquitous promoter such as the cytomegalovirus enhancer/chicken beta actin (CAG) promoter, the cytomegalovirus enhancer/promoter (CMV), the PGK promoter and the SV40 early promoter. In a specific variant, the ubiquitous promoter is the CAG promoter. According to another variant, the promoter is a liver-specific promoter such as the alpha-1 antitrypsin promoter (hAAT), the transthyretin promoter, the albumin promoter and the thyroxine-binding globulin (TBG) promoter. In a specific variant, the liver-specific promoter is the hAAT liver-specific promoter of SEQ ID NO:4. In a further particular embodiment, the nucleic acid construct comprised into the genome of the AAV vector of the invention further comprises an intron as described above, such as an intron placed between the promoter and the nucleic acid sequence encoding the UGT1A1 protein. Representative introns that may be included within the nucleic acid construct introduced within the AAV vector genome include, without limitation, the human beta globin b2 (or HBB2) intron, the FIX intron and the chicken beta-globin intron. Said intron within the genome of the AAV vector may be a classical (or unmodified) intron or a modified intron designed to decrease the number of, or even totally remove, alternative open reading frames (ARFs) within said intron. Modified and unmodified introns that may be used in the practice of this embodiment where the nucleic acid of the invention is introduced within an AAV vector are thoroughly described above. In a particular embodiment, the AAV vector, in particular the AAV8 vector, of the invention includes within its genome a modified (or optimized) intron such as the modified HBB2 intron of SEQ ID NO:7, the modified FIX intron of SEQ ID NO:8 and the modified chicken beta-globin intron of SEQ ID NO:10.

The invention also relates to a cell, for example a liver cell, that is transformed with a nucleic acid sequence of the invention. Cells of the invention may be delivered to the subject in need thereof via injection in the liver or in the bloodstream of said subject. In a particular embodiment, the invention involves introducing the nucleic acid sequence of the invention into liver cells, in particular into liver cells of the subject to be treated, and administering said liver cells into which the nucleic acid has been introduced to the subject.

The invention also provides a pharmaceutical composition, comprising an active agent selected from a nucleic acid of the invention, a vector of the invention or a cell of the invention, in combination with a pharmaceutically acceptable carrier.

The invention also relates to a method for the treatment of a hyperbilirubinemia caused by a mutation in the UGT1A1 gene, which comprises a step of delivering the nucleic acid, the vector, the pharmaceutical composition or the cell of the invention to a subject in need thereof. In a particular embodiment, the hyperbilirubinemia is CN syndrome type I or II, or Gilbert syndrome.

The invention also relates to the nucleic acid, the vector, the pharmaceutical composition or the cell of the invention for use as a medicament.

The invention also relates to the nucleic acid, the vector, the pharmaceutical composition or the cell of the invention, for use in a method for the treatment of a hyperbilirubinemia caused by a mutation in the UGT1A1 gene, in particular in a method for the treatment of CN syndrome type I or II, or of Gilbert syndrome.

The invention further relates to the use of the nucleic acid, the vector, the pharmaceutical composition or the cell of the invention, in the manufacture of a medicament useful for the treatment of a hyperbilirubinemia caused by a mutation in the UGT1A1 gene, in particular for the treatment of CN syndrome type I or II, or of Gilbert syndrome.

DETAILED DESCRIPTION OF THE INVENTION

The term "UGT1A1" refers to the wild-type *Homo sapiens* UDP-glycosyltransferase 1 family 1, polypeptide A, (UGT1A1) cDNA shown in SEQ ID NO:1 (accession number NM_000463.2, that is the reference sequence for the CDS of the mRNA for UGT1A1 human; OMIM reference 191740).

The term "codon optimized" means that a codon that expresses a bias for human (i.e. is common in human genes but uncommon in other mammalian genes or non-mammalian genes) is changed to a synonymous codon (a codon that codes for the same amino acid) that does not express a bias for human. Thus, the change in codon does not result in any amino acid change in the encoded protein.

The sequences shown in SEQ ID NO:2 or SEQ ID NO:3, in particular the sequence shown in SEQ ID NO:2, are preferred embodiments of the codon optimized nucleic acid sequence of the invention.

The change in the DNA sequence deriving from the codon optimization in SEQ ID NO:2 and SEQ ID NO:3 results in about 5% and about 10% increase of GC content in the UGT1A1 sequence, respectively.

Also encompassed by the invention is a nucleic acid sequence of the invention encoding a codon optimized human UGT1A1 protein that is "substantially identical", i.e. about 70% identical, more preferably about 80% identical, even more preferably about 90% identical, even more preferably about 95% identical, even more preferably about 97%, 98% or even 99% identical to the sequence SEQ ID NO: 2 or SEQ ID NO: 3.

"Identical" refers to the sequence identity between two nucleic acid molecules. When a position in both of the two compared sequences is occupied by the same base e.g., if a position in each of two DNA molecules is occupied by adenine, then the molecules are identical at that position. The percent of identity between two sequences is a function of the number of matching positions shared by the two sequences divided by the number of positions compared× 100. For example, if 6 of 10 of the positions in two sequences are matched then the two sequences are 60% identical. Generally, a comparison is made when two sequences are aligned to give maximum identity. Various bioinformatic tools known to the one skilled in the art might be used to align nucleic acid sequences such as BLAST or FASTA.

The term "decreased immunogenicity" as applied to the codon-optimized UGT1A1 coding sequence or to the modified intron of the invention means that this codon-optimized gene or modified intron comprises a decreased number of potential alternative open reading frames (or ARFs) in either the intron, or the coding sequence, or both, thereby limiting the number of potential translation protein by-products, in particular from the coded mRNA, as compared to the wild-type cDNA or other UGT1A1 cDNA variants. In particular, decreased ARFs are those whose length spans over 50 bp and have a stop codon in frame with a start codon.

In the context of the present invention, the term "gene therapy" refers to treatment of a subject which involves delivery of a gene/nucleic acid into an individual's cells for the purpose of treating a disease. Delivery of the gene is generally achieved using a delivery vehicle, also known as a vector. Viral and non-viral vectors may be employed to deliver a gene to a patient's cells. Particularly preferred are AAV vectors, in particular an AAV8 vector.

It will be appreciated that the nucleic acid of the invention may include one or more polyadenylation signals, typically located at the 3'-end of the molecule.

A preferred vector for delivering the nucleic acid of the invention is a viral vector, such as a retroviral vector, for example a lentiviral vector, or a non-pathogenic parvovirus, more preferably an AAV vector. The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter).

Therefore AAV has arisen considerable interest as a potential vector for human gene therapy. Among the favorable properties of the virus are its lack of association with any human disease, its ability to infect both dividing and non-dividing cells, and the wide range of cell lines derived from different tissues that can be infected.

Among the serotypes of AAVs isolated from human or non-human primates (NHP) and well characterized, human serotype 2 is the first AAV that was developed as a gene transfer vector. Other currently used AAV serotypes include AAV1, AAV3, AAV4, AAV5, AAV6, AAV7, AAV8, AAV9, AAVrh10, AAVrh74 and AAVdj, etc. In addition, non-natural engineered variants and chimeric AAV can also be useful.

AAVs may be engineered using conventional molecular biology techniques, making it possible to optimize these particles for cell specific delivery of nucleic acid sequences, for minimizing immunogenicity, for tuning stability and particle lifetime, for efficient degradation, and for accurate delivery to the nucleus.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

AAV-based recombinant vectors lacking the Rep protein integrate with low efficacy into the host's genome and are mainly present as stable circular episomes that can persist for years in the target cells.

Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

Accordingly, the present invention relates to an AAV vector comprising the nucleic acid of the invention, which is a codon-optimized UGT1A1 coding sequence. In the context of the present invention, the AAV vector comprises an AAV capsid able to transduce the target cells of interest, in particular hepatocytes. According to a particular embodiment, the AAV vector is of the AAV-1, -2, -5, -6, -7, -8, -9, -rh10, -rh74, -dj, etc., serotype. In a further particular embodiment, the AAV vector is a pseudotyped vector, i.e. its genome and capsid are derived from AAVs of different serotypes. For example, the pseudotyped AAV vector may be a vector whose genome is derived from the AAV1, 2, 3, 4, 5, 6, 7, 8, 9, 10, rh10, rh74, or dj serotype, and whose capsid is derived from another serotype. For example, the genome of the pseudotyped vector may be derived from the AAV1, 2, 3, 4, 5, 6, 7, 10, rh10, rh74 or dj serotype, and its capsid is derived from the AAV8 or AAV9 serotype, in particular from the AAV8 serotype.

In another embodiment, the capsid is a modified capsid. In the context of the present invention, a "modified capsid" may be a chimeric capsid or capsid comprising one or more variant VP capsid proteins derived from one or more wild-type AAV VP capsid proteins.

In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in Shen et al., Molecular Therapy, 2007 and in Tenney et al., Virology, 2014. For example a chimeric AAV vector can derive from the combination of an AAV8 capsid sequence with a sequence of the AAV1, 2, 3, 4, 5, 6, 7, 9, 10, rh10, rh74, or dj serotype. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in Bartel et al., 2011). In addition, capsid variants may include single amino acid changes such as tyrosine mutants (e.g. as described in Zhong et al., 2008).

In addition, the genome of the AAV vector may either be a single stranded or self-complementary double-stranded genome (McCarty et al., Gene Therapy, 2003). Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers. In a preferred embodiment, the AAV vector implemented in the practice of the present invention has a single stranded genome, and further preferably comprises an AAV8, AAV2 or AAV5 capsid, more preferably an AAV8 capsid.

Apart from the specific delivery systems embodied below in the examples, various delivery systems are known and can be used to administer the nucleic acid of the invention, e.g., encapsulation in liposomes, microparticles, microcapsules, recombinant cells capable of expressing the codon-optimized UGT1A1 coding sequence, receptor-mediated endocytosis, construction of a therapeutic nucleic acid as part of a retroviral or other vector, etc. Methods of administration of the nucleic acid include but are not limited to intradermal, intramuscular, intraperitoneal, intravenous, subcutaneous, intranasal, epidural, and oral routes. The nucleic acid sequence of the invention, whether vectorized or not, may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the liver of the subject by any suitable route. In addition naked DNA such as minicircles and transposons can be used for delivery or lentiviral vectors. Additionally, gene editing technologies such as zinc finger nucleases, meganucleases, TALENs, and CRISPR can also be used to deliver the coding sequence of the invention.

In a specific embodiment, it may be desirable to administer the pharmaceutical compositions of the invention locally to the area in need of treatment, i.e. the liver. This may be achieved, for example, by means of an implant, said implant being of a porous, nonporous, or gelatinous material, including membranes, such as sialastic membranes, or fibers.

In another embodiment, the nucleic acid of the invention can be delivered in a vesicle, in particular a liposome In yet another embodiment, the nucleic acid of the invention can be delivered in a controlled release system.

The present invention also provides pharmaceutical compositions comprising a nucleic acid of the invention, or the vector of the invention, or the cell of the invention. Such compositions comprise a therapeutically effective amount of the therapeutic (the nucleic acid, vector or cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents or pH buffering agents. These compositions can take the form of solutions, suspensions, emulsions, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject. In a particular embodiment, the nucleic acid, vector or cell of the invention is formulated in a composition comprising phosphate-buffered saline and supplemented with 0.25% human serum albumin. In another particular embodiment, the nucleic acid, vector or cell of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic, such as lignocaine, to ease pain at the site of the injection.

The amount of the therapeutic (i.e. a nucleic acid, vector or cell) of the invention which will be effective in the treatment of CN syndrome can be determined by standard clinical techniques. In addition, in vivo and/or in vitro assays may optionally be employed to help predict optimal dosage ranges. The precise dose to be employed in the formulation will also depend on the route of administration and the seriousness of the disease, and should be decided according to the judgment of the practitioner and each patient's circumstances. The dosage of the nucleic acid, the vector or the cell administered to the subject in need thereof will vary based on several factors including, without limitation, the route of administration, the specific disease treated, the subject's age or the level of expression necessary to required the therapeutic effect. One skilled in the art can readily determine, based on their knowledge in this field, the dosage range required based on these factors and others. In case of a treatment comprising administering a viral vector, such as an AAV vector, to the subject, typical doses of the vector are of at least $1\times10^8$ vector genomes per kilogram body weight (vg/kg), such as at least $1\times10^9$ vg/kg, at least $1\times10^{10}$ vg/kg, at least $1\times10^{11}$ vg/kg, at least $1\times10^{12}$ vg/kg at least $1\times10^{13}$ vg/kg, or at least $1\times10^{14}$ vg/kg.

Figure 1:
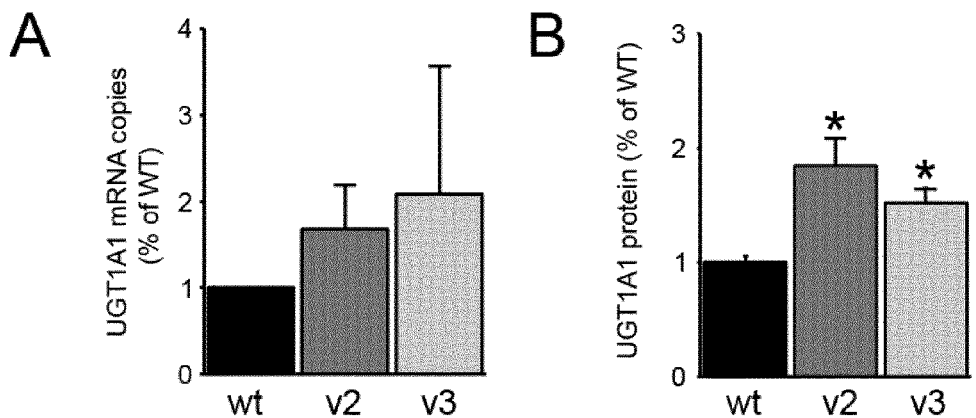
FIG. 1 includes graphs showing the levels of messenger RNA observed in Huh-7 cells transfected with plasmid expressing wild-type UGT1A1 or two codon optimized UGT1A1 sequences (panel A) and the quantification by western blot of UGT1A1 protein in the same samples (panel B).

Ranges: Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The disclosures of each and every patent, patent application, and publication cited herein are hereby incorporated herein by reference in their entirety.

Without further description, it is believed that one of ordinary skill in the art can, using the preceding description and the following illustrative examples, make and utilize the compounds of the present invention and practice the claimed methods.

Examples

The invention is further described in detail by reference to the following experimental examples and the attached figures. These examples are provided for purposes of illustration only, and are not intended to be limiting.

Material and Methods

Codon Optimization and AAV Vector Construct:

The UGT1A1 underwent codon optimization according to several different algorithms. Additionally, removal of cryptic transcription start sites was implemented throughout the construct. The resulting constructs were either introduced into expression plasmids, or packaged into AAV serotype 8 vectors and tested in vitro and in vivo (rats and mice) for potency.

The following abbreviations are used throughout this experimental part for these constructs:

WT.0: wild-type UGT1A1 transgene and the wild-type HBB2 intron (SEQ ID NO:5);

WT: wild-type UGT1A1 transgene and the optimized version of the HBB2 intron with some ARFs removed (SEQ ID NO:6);

v2 (or v2.0): comprises codon-optimized UGT1A1 transgene version 2.0 (SEQ ID NO:2) and the wild-type HBB2 intron (SEQ ID NO:5);

v2.1: comprises codon-optimized UGT1A1 transgene version 2.0 (SEQ ID NO:2) and an optimized version of the HBB2 intron with some ARFs removed (SEQ ID NO:6);

v3: comprises codon-optimized UGT1A1 transgene version 3 (SEQ ID NO:3) with an optimized version of the HBB2 intron with some ARFs removed (SEQ ID NO:6).

AAV8-hAAT-wtUGT1A1: AAV8 vector containing the WT construct, under the control of an hAAT promoter wild-type UGT1A1 transgene;

AAV8-hAAT-coUGT1A1v2: AAV8 vector containing the v2 construct, under the control of an hAAT promoter;

AAV8-hAAT-coUGT1A1v2.1: AAV8 vector containing the v2.1 construct, under the control of an hAAT promoter; and AAV8-hAAT-coUGT1A1v3: AAV8 vector containing the v3 construct, under the control of an hAAT promoter wild-type.

In Vitro Assay:

The human hepatocyte cell line Huh7 was transduced at increasing multiplicity of infection (MOI) of 0, 5000 (5), 10000 (10), or 25000 (25) or transfected with the indicated plasmid vectors and lipofectamine. Forty-eight hours after transduction cells were harvested, lysed and microsomal extracts were prepared and loaded on a western blot, where a polyclonal antibody against human UGT1 was used to detect the protein. The constitutively expressed protein calnexin was used as loading control.

A portion of the cells used for microsomal preparation has been used for mRNA extraction with trizol. Extracted mRNA has been treated with DNAse, retrotranscribed and analyzed by RT-PCR with oligonucleotide primers specific for UGT1A1 sequence. Oligonucleotide primers specific for human serum alkaline phosphatase have been used for the normalization.

In Silico Analysis:

The alternative reading frame (ARF) analysis has been performed on the coding strand of the two UGT1A1 sequences with the ORF analysis tool present in the Vector NTI software (Life Technologies). Classic start and stop sites for eukaryotic cells were utilized (respectively ATG as start site and TAA TGA TAG as stop sites). ARFs were considered when their length spans over 50 bp and they have a stop codon in frame with the start.

Animals:

Gunn rats, which present a deficiency in the UGT1A1 gene, were injected with vectors at an age of 6-8 weeks. Vectors were delivered via the tail vein in a volume of 0.5 ml. Serum samples were collected weekly to monitor levels of total bilirubin (TB). Untreated affected animals and wild type or healthy littermates were used as controls.

Ugt1 mutant mice in C57Bl/6 background have been generated previously (Bortolussi et al., 2012). WT littermates were used as a control. Mice were housed and handled according to institutional guidelines, and experimental procedures approved by the local Ethical Committee and the relevant regulatory authorities, with full respect to the EU Directive 2010/63/EU for animal experimentation. The genetic mutation in the Ugt1a gene was transferred to FVB/NJ mouse strain. Animals used in this study were at least 99.8% C57Bl/6 mice or FVB/NJ genetic background, obtained after more than 9 backcrosses with C57Bl/6 mice and FVB/NJ, respectively. Mice were kept in a temperature-controlled environment with 12/12 hours light-dark cycle. They received a standard chow diet and water ad libitum. Vectors were injected intraperitoneally at day 2 (P2) after birth and bilirubin levels were assayed 4 weeks after the injection of the vector.

AAV Doses:

The doses of vector administered were indicated in the figure legends.

Serum Preparation for Rats:

Blood samples were collected weekly by puncture in retro-orbital sinus, in dry syringes. Blood was centrifuged at 8000 rpm at 4° C., aliquoted and frozen at −20° C.

Plasma Preparation for Mice:

Blood samples were collected at 4 weeks after injection in mutant and WT littermates by cardiac puncture in EDTA-collecting syringes. Blood was centrifuged at 2500 rpm, plasma was collected, aliquoted and frozen at −80° C. All procedures were performed in dim light to avoid bilirubin degradation.

Bilirubin Determination for Rats:

Total bilirubin determination in serum was performed using Bilirubin Assay Kit (Abnova, ref. KA1614), as described by the manufacturers. We used a volume of 504, of serum to perform the analysis. Absorbance values at 530 nm were obtained by using a multiplate reader (PerkinElmer EnSpire)

Bilirubin Determination for Mice:

Total bilirubin determination in plasma was performed using Direct and Total Bilirubin Reagent kit (BQ Kits, San Diego, Calif.), as described by the manufacturers with minor modifications: the reaction was scaled down and it was performed in a final volume of 300 µl (instead of 6000 µl), with only 10 µl of plasma. Three commercial bilirubin reference standards (Control Serum I, Control Serum II and Bilirubin Calibrator, Diazyme Laboratories, Poway, Calif., USA) were included in each set of analysis as quality control. Absorbance values at 560 nm were obtained by using a multiplate reader (Perkin Elmer Envision Plate Reader, Waltham, Mass., USA).

Western Blot on Liver Extracts:

Snap-frozen liver obtained from the animals injected with either one of the three vectors have been rapidly homogenized. Homogenates have been used for microsome preparation. Microsomal extracts were then loaded on a western blot, where a polyclonal antibody against human UGT1 was used to detect the protein. Protein bands were quantified.

Results

Codon-optimized versions of the human UGT1A1 coding sequence were produced and introduced into an expression plasmid. The two optimized UGT1A1 coding sequences (v2 and v3 sequences) and the wild-type sequence have been transfected in Huh-7 cells. Results obtained are reported in FIG. 1. This experiment shows that the two codon optimized sequences are more efficiently translated than the wild-type sequence in human cells in vitro.

Figure 2:
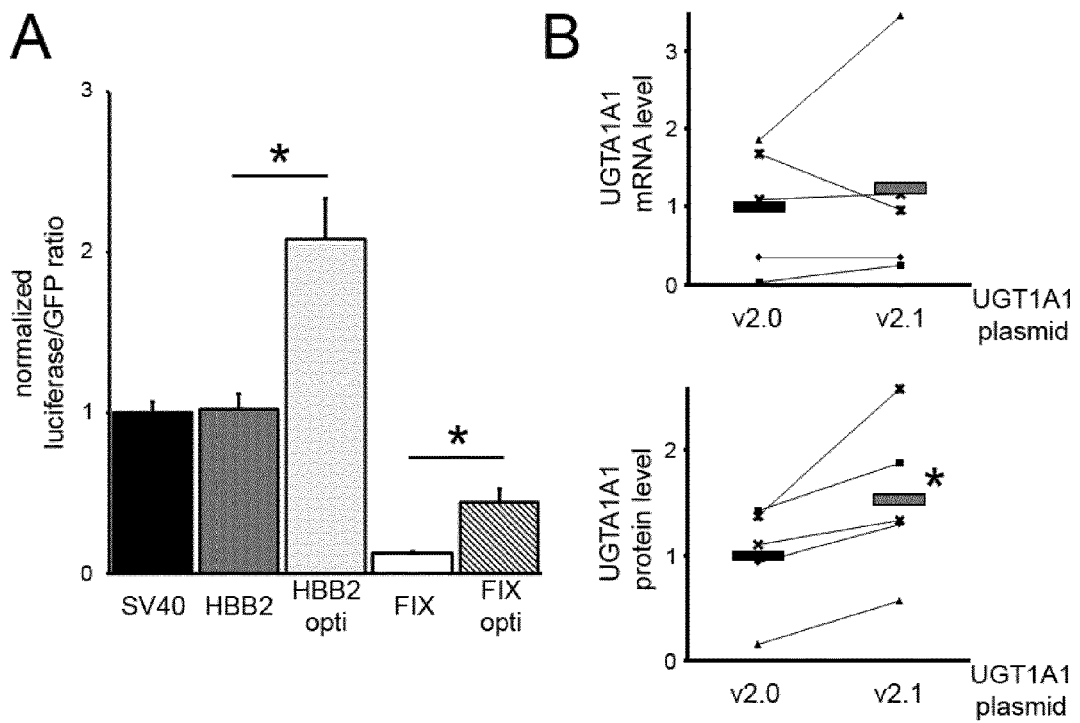
FIG. 2 includes graphs showing the effect of different intron optimization in the expression of luciferase (panel A) and the effect of HBB2 optimization on UGT1A1 RNA and protein expression level (panel B).

In FIG. 2 panel A are shown luciferase levels produced in Huh-7 cells by transfection with plasmids expressing luciferase under the transcriptional control of the hAAT promoter. Different intronic sequences have been cloned at the 5' of the luciferase coding sequence. Two of them, namely HBB2 and FIX introns, were optimized by removal of ARFs in the sequence done by replacing one nucleotide in ATG codons identified in the wild-type sequence of said introns. The expression of the optimized construct in a hepatic cell line indicates that the removal of ARFs from the intronic sequences increased luciferase expression in vitro in both cases, with the optimized HBB2 intron being particularly potent. In panel B two plasmids were compared, both expressing UGT1A1 under the transcriptional control of the hAAT promoter. V2.0 contains the wild-type HBB2 intron whereas v2.1 contains the optimized version. Data shown indicates that v2.1 plasmid expresses 50% more UGT1A1 than v2.0 without any increase in the mRNA levels.

Figure 3:
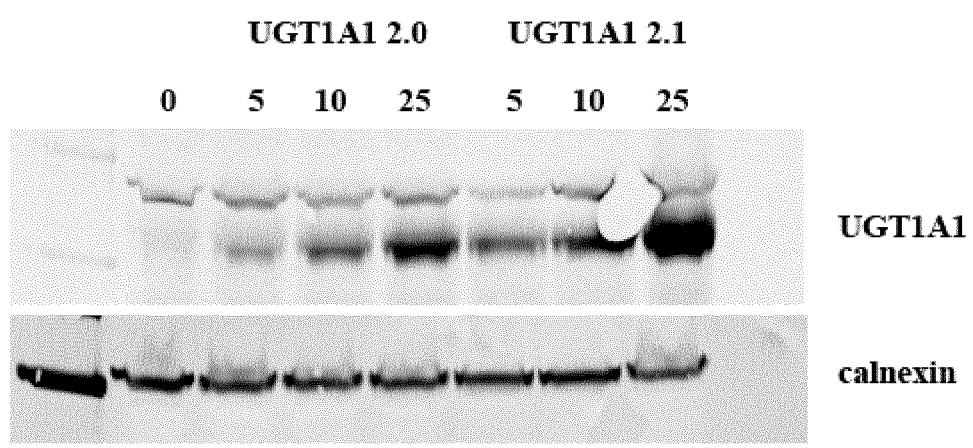
FIG. 3 is a photograph of a western blot gel showing the expression of UGT1A1 protein from two vectors containing a codon-optimized UGT1A1 coding sequence and containing either the wild-type (UGT1A1 2.0) or an optimized (UGT1A1 2.1) HBB2 intron.

Codon-optimized UGT1A1 version 2.0 and 2.1 AAV8 vectors (UGT1A1 2.0 and UGT1A1 2.1, respectively) were tested in vitro. UGT1A1 2.0 and UGT1A1 2.1 vectors differ only by the fact that they contain the wild-type HBB2 intron (SEQ ID NO:5) or a modified HBB2 intron where ARFs have been removed (SEQ ID NO:6), respectively. Results obtained are reported in FIG. 3. This experiment shows that the codon-optimized UGT1A1 vector version 2.1 is more potent than the 2.0 version in human cells in vitro.

Figure 4:
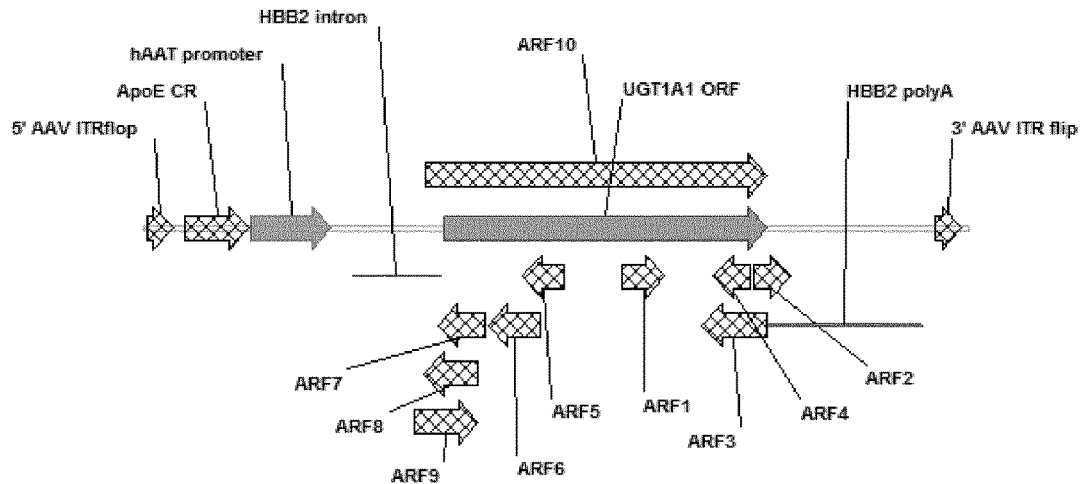
FIG. 4 is a schematic representation of the in silico analysis of alternate reading frame (ARF) within the wild-type UGT1A1 (A) and a codon-optimized UGT1A1 v2.1 (B) vectors.
Figure 4:
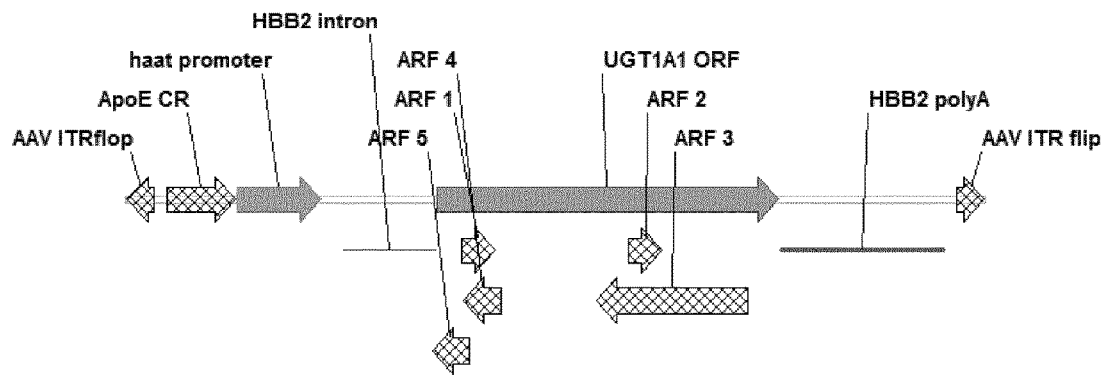

FIG. 4 shows the result of the in silico analysis of alternate reading frame (ARF) within the wild-type UGT1A1 (A) and the codon-optimized UGT1A1v2.1 (B) vectors. The v2.1 vector has only a limited number of ARFs compared to the wild type sequence and mostly in reverse orientation with respect to the promoter. In addition, we can see in FIG. 4 the ARF9 and 10 that are normally present in the HBB2 intron (used in the wild-type UGT1A1 construct represented in A) have been removed from the modified HBB2 intron of SEQ ID NO:6 introduced in the UGT1A1v2.1 optimized vector.

Figure 5:
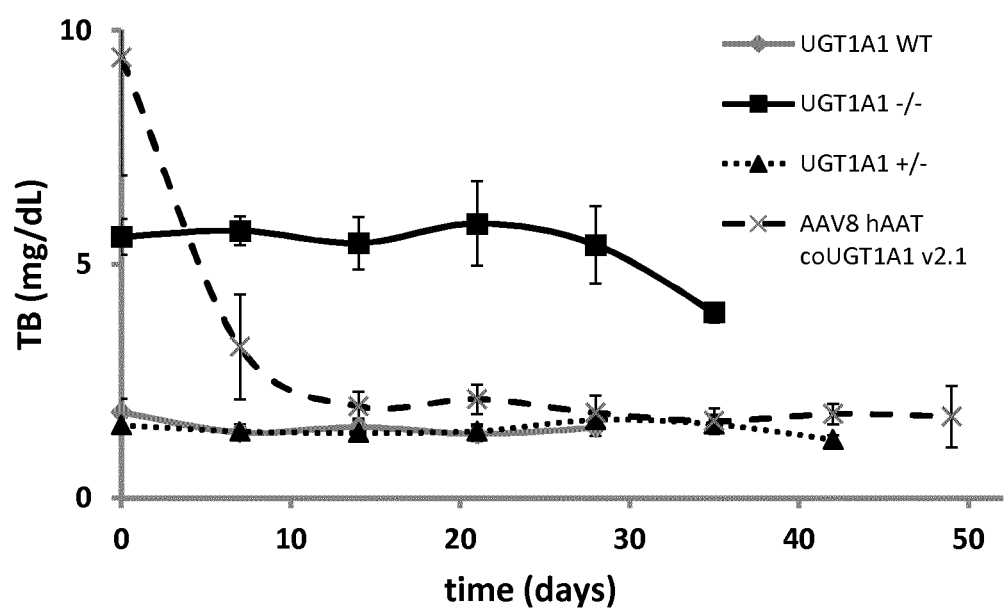
FIG. 5 is a graph showing the levels of total bilirubin (TB) measured every week after the injection of a codon-optimized UGT1A1 vector or of PBS in different rat strains.

Then, the codon-optimized AAV8-hAAT-coUGT1A1v2.1 vector was administered at a dose of $5 \times 10^{12}$ vg/kg. Tail vein injection of the vector has been performed in 6-week-old homozygous Gunn rats (UGT1A1−/−). In the graph of FIG. 5 are shown the levels of total bilirubin (TB) measured every week, after the injections and in PBS-injected wild type (WT, gray line), heterozygous (UGT1A1+/−, dotted line) and homozygous (black line) Gunn rats. All data are expressed as mean±SE. Injection of the codon-optimized vector resulted in complete correction of the disease phenotype.

Figure 6:
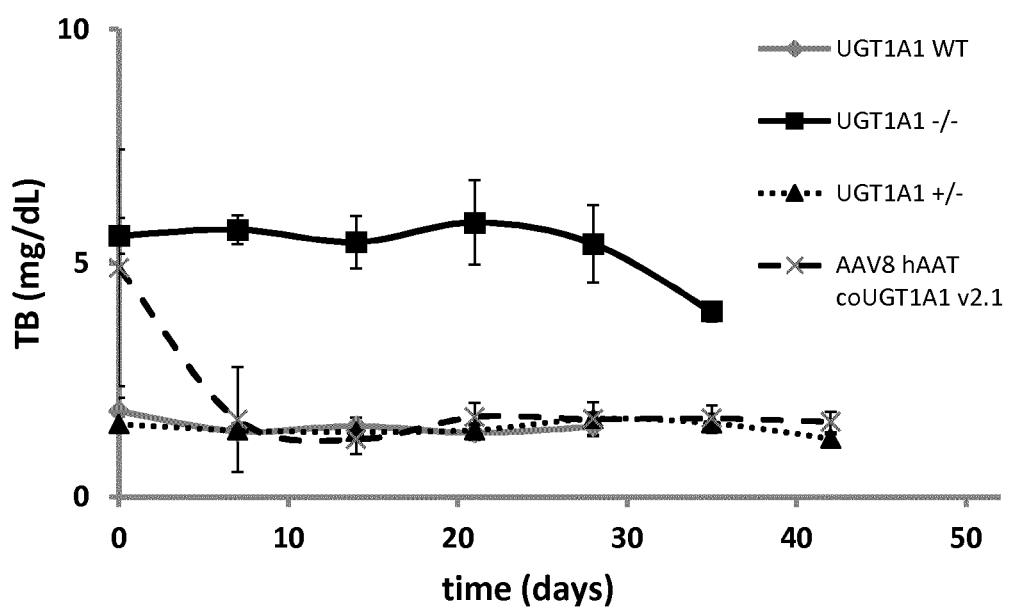
FIG. 6 is a graph showing the levels of total bilirubin (TB) measured every week after the injection of a lower dose of codon-optimized UGT1A1 vector (as compared to the data reported in FIG. 5) or of PBS in different rat strains.

The AAV8-hAAT-UGT1A1v2.1 vector was also administered at a dose of $5\times10^{11}$ vg/kg. Vector was administered by tail vein injection in 6-week-old homozygous Gunn rats (UGT1A1−/−). In the graph of FIG. 6 are shown the levels of total bilirubin (TB) measured every week, after the injections and in PBS-injected wild type (WT, gray line), heterozygous (UGT1A1+/−, dotted line) and homozygous (black line) Gunn rats. All data are expressed as mean±SE. Injection of the codon-optimized vector resulted in complete correction of the disease phenotype.

Figure 7:
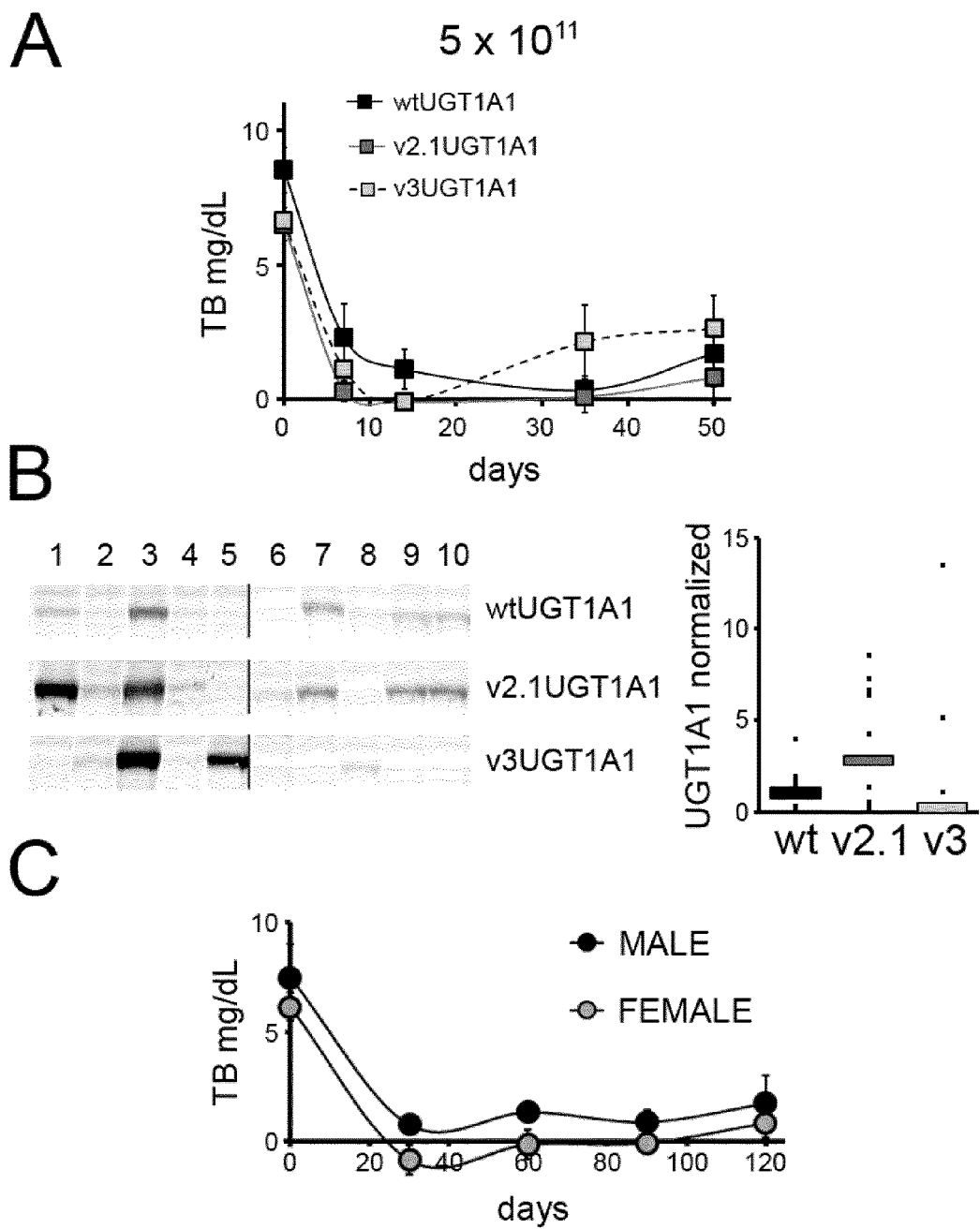
FIG. 7 includes (A) a graph showing levels of total bilirubin (TB) measured every week after the injection of the three UGT1A1 vectors (as compared to the data reported in FIG. 8); (B) a photograph of a western blot of liver extracts obtained from rats treated with the three vectors and their relative quantification; and (C) a graph presenting the long term evaluation of the efficacy of AAV8-v2.1 UGT1A1 four months after the injection in both male and female animals.

The two codon-optimized (v2.1 and v3) and the wild-type AAV8-hAAT-UGT1A1 vectors were further administered at a dose of $5\times10^{11}$ vg/kg. Tail vein injection of the vector has been performed in 6-week-old homozygous Gunn rats (UGT1A1−/−). In the graph of FIG. 7A are shown the levels of total bilirubin (TB) measured every week, after the injections. All data are expressed as mean±SE. As shown in FIG. 7 panel A, the injection of the three vectors resulted in complete correction of the disease phenotype. Two months after the injection, animals were sacrificed and the level of UGT1A1 protein has been quantified by western blot in liver homogenates. In panel B are showed the photographs of western blot with an antibody specific for UGT1A1 protein. The quantification of the bands showed an increase in the quantity of UGT1A1 protein in rats treated with AAV8-hAAT-coUGT1A1v2.1 even if the difference is not significant due to the high variability of the expression levels observed in the different animals.

Long term efficacy has been evaluated in two month old Gunn rats injected with $5\times10^{12}$ vg/kg of AAV8-v2.1 UGT1A1 vector. Four months after the injection average bilirubin level in blood is 1.75 mg/dL (initial level at D0: 7.49, reduction 77%) in male rats and 0.85 mg/dL (initial level at D0: 6.15 mg/dL, reduction 86%) in female rats. This result, that indicates a long term correction of the phenotype, is particularly striking as compared to a previous study of Pastore et al. reporting a reduction in female rats of only 50% of baseline bilirubin levels using a different construct. Taken together the data showed indicates that the inventive process applied to AAV8-hAAT-coUGT1A1v2.1 resulted in a vector with a better in vivo efficacy as compared to other vectors developed to cure CN.

Figure 8:
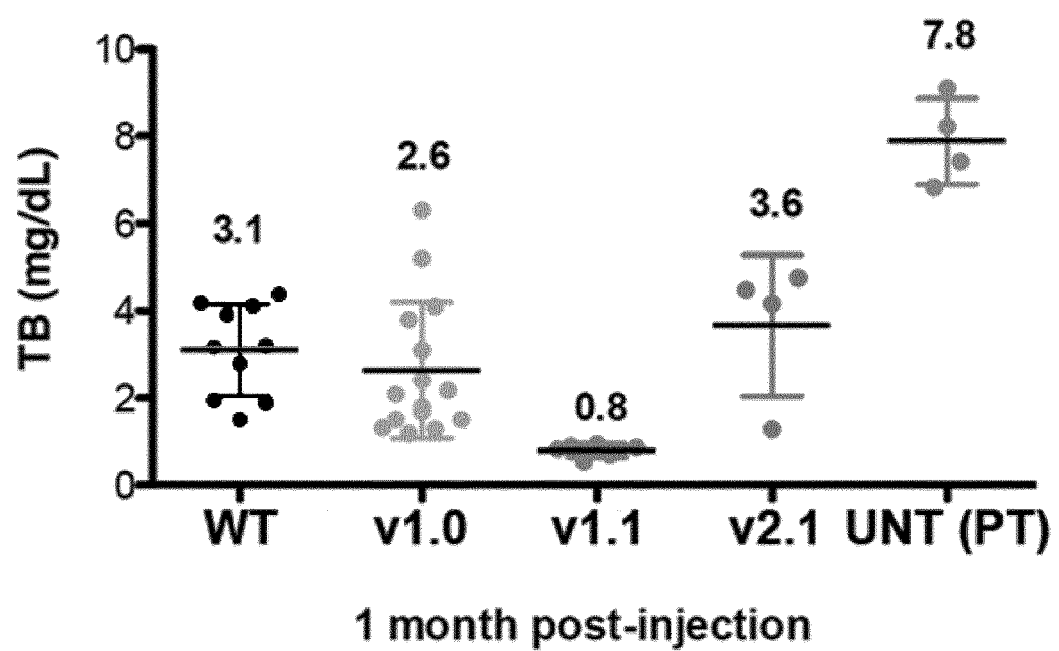
FIG. 8 is a graph showing the ability of different constructs to correct severe hyperbilirubinemia (Total Bilirubin, expressed as mg/dl) in the mouse model of Crigler-Najjar syndrome. Untreated animals (UNTR) are reported.

We also tested the efficacy of correction of total bilirubin in the mouse model of Crigler-Najjar syndrome. FIG. 8 is a graph showing Total Bilirubin (TB) levels at 1 month post-injection. Animals were injected at day 2 after birth (P2) with a dose of 3E10 vg/mouse.

Untreated affected animals kept alive with 15 days-phototherapy were used as controls (UNTR (PT)).

This experiment shows that the version 2.1 vector gives the highest level of TB correction of all vectors. All data are expressed as mean±SD. Each dot represents a single animal.

REFERENCES

Allay et al., Hum Gene Ther. 2011 May; 22(5):595-604
Bartel et al., Front Microbiol. 2011 Oct. 4; 2:204
Bortolussi et al., FASEB J. 2012 March; 26(3):1052-63
McCarty et al., Gene Ther. 2003 December; 10(26):2112-8
Pastore et al., Mol Ther. 2013 May; Vol. 21; supplement 1; S192-3 (abstract No. 499)
Seppen et al., Mol Ther. 2006 June; 13(6):1085-92
Shen et al., Mol Ther. 2007 November; 15(11):1955-62
Tenney et al., Virology. 2014 April; 454-455:227-36
Zhong et al., Proc Natl Acad Sci USA. 2008 Jun. 3; 105(22):7827-32

The invention claimed is:

1. An isolated nucleic acid sequence comprising the nucleotide sequence as set forth in SEQ ID NO: 2 or SEQ ID NO: 3, wherein said isolated nucleic acid sequence encodes UDP-glucuronosyltransferase isozyme 1A1 (UGT1A1).

2. A nucleic acid construct comprising the nucleic acid sequence according to claim 1.

3. The nucleic acid construct according to claim 2, wherein said nucleic acid construct is an expression cassette comprising said nucleic acid sequence operably linked to a promoter.

4. The nucleic acid construct according to claim 3, wherein the promoter is a liver-specific promoter.

5. The nucleic acid construct according to claim 3, wherein the promoter is selected from the group consisting of the alpha-1 antitrypsin promoter (hAAT), the transthyretin promoter, the albumin promoter and the thyroxine-binding globulin (TBG) promoter.

6. The nucleic acid construct according to claim 3, said nucleic acid construct further comprising an intron.

7. The nucleic acid construct according to claim 6, wherein the intron is selected from the group consisting of a human beta globin b2 (HBB2) intron, a FIX intron and a chicken beta-globin intron.

8. The nucleic acid construct according to claim 6, wherein the intron is a sequence modified intron having decreased or no alternative open reading frames (ARFs).

9. The nucleic acid construct according to claim 8, wherein said sequence modified intron consists of the nucleotide sequence as set forth in SEQ ID NO: 6, SEQ ID NO: 8 or SEQ ID NO: 10.

10. A vector comprising the nucleic acid sequence of claim 1.

11. The vector according to claim 10, wherein said vector is a viral vector.

12. The vector according to claim 10, wherein said viral vector is a retroviral vector, a single-stranded AAV vector or double-stranded self-complementary AAV vector.

13. The vector according to claim 11, wherein the AAV vector has an AAV-derived capsid selected from the group consisting of an AAV-1, -2, -5, -6, -7, -8, -9, -rh10, -rh74, -dj capsid and chimeric capsid.

14. The vector according to claim 12, wherein the AAV vector has an AAV8 capsid.

15. The vector according to claim 12, wherein the AAV vector is a pseudotyped AAV vector.

16. An isolated cell comprising the nucleic acid sequence according to claim 1.

17. The cell according to claim 16, wherein said cell is a liver cell or a muscle cell.

18. The isolated nucleic acid sequence according to claim 1, wherein said nucleic acid sequence comprises the nucleotide sequence as set forth in SEQ ID NO: 2.

19. The isolated nucleic acid sequence according to claim 1, wherein said nucleic acid sequence comprises the nucleotide sequence as set forth in SEQ ID NO: 3.

* * * * *

UNITED STATES PATENT AND TRADEMARK OFFICE
CERTIFICATE OF CORRECTION

PATENT NO. : 10,471,132 B2
APPLICATION NO. : 15/303834
DATED : November 12, 2019
INVENTOR(S) : Federico Mingozzi et al.

Page 1 of 1

It is certified that error appears in the above-identified patent and that said Letters Patent is hereby corrected as shown below:

In the Specification

Column 4,
Line 39, "thrombocytopenia, congenital" should read --thrombocytopenia, X-linked congenital--.

Column 13,
Line 64, "of 504," should read --of 50µL--.

Signed and Sealed this
Sixteenth Day of June, 2020

Andrei Iancu
*Director of the United States Patent and Trademark Office*

SEQUENCE LISTING

<160> NUMBER OF SEQ ID NOS: 11

<210> SEQ ID NO 1
<211> LENGTH: 1602
<212> TYPE: DNA
<213> ORGANISM: homo sapiens

<400> SEQUENCE: 1

```
atggctgtgg agtcccaggg cggacgccca cttgtcctgg gcctgctgct gtgtgtgctg      60
ggcccagtgg tgtcccatgc tgggaagata ctgttgatcc cagtggatgg cagccactgg     120
ctgagcatgc ttggggccat ccagcagctg cagcagaggg acatgaaat agttgtccta     180 gcacctgacg cctcgttgta catcagagac ggagcatttt acaccttgaa gacgtaccct     240
gtgccattcc aaagggagga tgtgaaagag tcttttgtta gtctcgggca taatgttttt     300
gagaatgatt ctttcctgca gcgtgtgatc aaaacataca gaaaataaa aaaggactct     360 gctatgcttt tgtctggctg ttcccactta ctgcacaaca aggagctcat ggcctccctg     420
gcagaaagca gctttgatgt catgctgacg gacccttttcc ttccttgcag ccccatcgtg     480
gcccagtacc tgtctctgcc cactgtattc ttcttgcatg cactgccatg cagcctggaa     540
tttgaggcta cccagtgccc caaccccattc tcctacgtgc caggcctct ctcctctcat     600 tcagatcaca tgaccttcct gcagcgggtg aagaacatgc tcattgcctt tcacagaac     660
```

```
tttctgtgcg acgtggttta ttccccgtat gcaaccctttg cctcagaatt ccttcagaga    720
gaggtgactg tccaggacct attgagctct gcatctgtct ggctgtttag aagtgacttt    780
gtgaaggatt accctaggcc catcatgccc aatatggttt tgttggtgg aatcaactgc     840
cttcaccaaa atccactatc ccaggaattt gaagcctaca ttaatgcttc tggagaacat    900
ggaattgtgg ttttctcttt gggatcaatg gtctcagaaa ttccagagaa gaaagctatg    960
gcaattgcta atgctttggg caaaatccct cagacagtcc tgtggcggta cactggaacc   1020
cgaccatcga atcttgcgaa caacacgata cttgttaagt ggctacccca aaacgatctg   1080
cttggtcacc cgatgacccg tgcctttatc acccatgctg gttcccatgg tgtttatgaa   1140
agcatatgca atggcgttcc catggtgatg atgcccttgt ttggtgatca gatggacaat   1200
gcaaagcgca tggagactaa gggagctgga gtgaccctga atgttctgga aatgactct    1260
gaagatttag aaaatgctct aaaagcagtc atcaatgaca aaagttacaa ggagaacatc   1320
atgcgcctct ccagccttca caggaccgc ccggtggagc cgctggacct ggccgtgttc   1380
tgggtggagt ttgtgatgag gcacaagggc gcgccacacc tgcgcccgc agcccacgac   1440
ctcacctggt accagtacca ttccttggac gtgattggtt cctcttggc cgtcgtgctg    1500
acagtggcct tcatcacctt taaatgttgt gcttatggct accggaaatg cttggggaaa   1560
aaagggcgag ttaagaaagc ccacaaatcc aagacccatt ga                      1602
```

<210> SEQ ID NO 2
<211> LENGTH: 1602
<212> TYPE: DNA
<213> ORGANISM: artificial
<220> FEATURE:
<223> OTHER INFORMATION: optimized UGT1A1 v2.1

<400> SEQUENCE: 2

```
atggctgtgg aatcacaagg aggtagacca ctggttctcg acttttgct ttgcgtgctg      60
gggcccgtgg tgtcgcatgc cggaaagatc ctgctgatcc cggtggatgg atcacactgg    120
ctgtccatgc tgggtgccat ccaacagctc cagcagcggg gccacgaaat tgtggtcctg    180
gccccggacg cttccctgta tattcgggac ggagcgttct acactctcaa gacctaccct    240
gtccccttcc aaagggagga cgtgaaggaa agctttgtgt cgctggggca taatgtgttc    300
gagaacgaca gcttcctcca aagggttatt aaaacctaca gaaagatcaa aaaggattcg    360
gccatgctcc tttccggatg ttcacacctg ttgcataaca aggaattgat ggccagcctg    420
gcagaatcca gctttgacgt catgcttact gacccgttct tgccttgctc cccgattgtg    480
gcccaatacc tgtcgctccc aaccgtgttc ttcctgcacg ccttgccttg ttcgctggaa    540
ttcgaagcga ctcagtgtcc caatccgttc tcctacgtcc cgcgcccgct ttcaagccat    600
tcggatcaca tgactttcct ccagcgcgtc aagaacatgc tcattgcgtt cagccagaac    660
tttctgtgcg acgtggttta ctcaccttac gctaccttgg cttctgagtt cctgcagaga    720
gaagtgactg tgcaagatct gctgtcctca gcgtccgttt ggttgttccg gtctgacttc    780
gtcaaggact acccgcgccc gatcatgccg aatatggtct ttgtgggcgg tatcaactgc    840
ctgcatcaaa acccactgag ccaggagttt gaggcgtaca tcaacgcctc gggagagcat    900
ggaatcgtgg tgttctcccct cggttccatg gtgtccgaga tcccggaaaa gaaggcaatg    960
gccatcgcag atgccctggg caaaatcccg cagaccgtgc tctggcgcta cactgggtact  1020
cggcctagca atttggcaaa caacaccatc ctggtgaaat ggctgccgca gaacgacctc   1080
```

```
ctgggccacc caatgactcg cgctttcatt acccatgcgg gctcgcacgg agtctacgaa   1140
tccatctgca atggagtccc gatggtgatg atgccacttt tcggagatca gatggataat   1200
gcaaaaagaa tggaaaccaa gggggccgga gtgacgctga acgtgcttga aatgacctcg   1260
gaagatctgg agaacgctct caaagcggtg atcaacgaca agtcctacaa ggaaaacatc   1320
atgcgcctga gctccctcca aaggaccga ccagtggaac cgctggacct cgcggtcttt   1380
tgggtggagt tcgtgatgag gcacaagggc gccccccacc tcagacccgc agctcatgac   1440
ctcacttggt accagtacca ttcgctggat gtcatcggct ttctcctggc ggtcgtgctc   1500
accgtggcgt tcatcacctt caagtgctgc gcctacggat atcgcaaatg cttggggaag   1560
aaaggacggg tgaagaaggc acacaagtca aagacgcact ga                     1602

<210> SEQ ID NO 3
<211> LENGTH: 1602
<212> TYPE: DNA
<213> ORGANISM: artificial
<220> FEATURE:
<223> OTHER INFORMATION: optimized UGT1A1 v3

<400> SEQUENCE: 3
atggccgtgg aatctcaggg cggcagacct ctggtgctgg gcctgctgct gtgtgtgctg     60
ggacctgtgg tgtctcacgc cggcaagatc ctgctgatcc cgtggatgg cagccactgg    120
ctgtctatgc tgggcgccat tcagcagctg cagcagaggg ccacgagat cgtggtgctg    180
gcccctgatg ccagcctgta catcagagat ggcgccttct acaccctgaa aacctacccc    240
gtgcccttcc agcgcgagga cgtgaaagaa agcttcgtgt ccctgggcca caacgtgttc    300
gagaacgaca gcttcctgca gagagtgatc aagacctaca gaagatcaa gaaagacagc    360
gccatgctgc tgagcggctg ctcccatctg ctgcacaaca agaactgat ggcctccctg    420
gccgagagca gcttcgacgt gatgctgacc gacccattcc tgccctgcag ccctatcgtg    480
gcccagtacc tgagcctgcc tacgtgttc ttcctgcacg ccctgccttg ctccctggaa    540
ttcgaggcca cccagtgccc caacccttc agctacgtgc ccagaccact gagcagccac    600
agcgaccaca tgacctttct gcagcgcgtg aagaacatgc tgatcgcctt cagccagaac    660
ttcctgtgcg acgtggtgta cagcccctac gctaccctgg ccagcgaatt cctgcagcgg    720
gaagtgaccg tgcaggacct gctgtctagc gccagcgtgt ggctgttccg cagcgacttc    780
gtgaaggact accccagacc catcatgccc aacatggtgt tcgtgggcgg catcaactgc    840
ctgcaccaga ccccctgag ccaggaattt gaggcctaca tcaacgccag cggcgagcac    900
ggcatcgtgg tgtttagcct gggcagcatg gtgtccgaga tccccgagaa aaaggccatg    960
gctatcgccg acgccctggg aaagatccc cagacagtgc tgtggcggta caccggcacc   1020
agacccagca acctggccaa caacaccatc ctcgtgaaat ggctgcccca gaacgacctg   1080
ctgggccacc ctatgacccg ggccttatc acacacgccg gctcccatgg cgtgtacgag   1140
agcatctgca acgcgtgcc catggtcatg atgcccctgt cggcgacca gatggacaac   1200
gccaagcgga tggaaacaaa gggcgctggc gtgaccctga acgtgctgga aatgaccagc   1260
gaggacctga aaacgccct gaaggccgtg atcaacgaca gagctacaa agaaaacatc   1320
atgcggctgt ccagcctgca aggacaga cccgtggaac ccctggacct ggccgtgttc   1380
tgggtggaat tcgtgatgcg gcacaagggc gctccccatc tgaggcctgc agctcacgac   1440
ctgacctggt atcagtacca cagcctggac gtgatcggct tcctgctggc agtggtgctg   1500
accgtggcct tcatcacctt caagtgctgc gcctacggct accggaagtg cctgggcaag   1560
```
aaaggcagag tgaagaaggc ccacaagagc aagacccact ga           1602

<210> SEQ ID NO 4
<211> LENGTH: 397
<212> TYPE: DNA
<213> ORGANISM: homo sapiens

<400> SEQUENCE: 4
gatcttgcta ccagtggaac agccactaag gattctgcag tgagagcaga gggccagcta    60
agtggtactc tcccagagac tgtctgactc acgccacccc ctccaccttg gacacaggac   120
gctgtggttt ctgagccagg tacaatgact cctttcggta agtgcagtgg aagctgtaca   180
ctgcccaggc aaagcgtccg ggcagcgtag gcgggcgact cagatcccag ccagtggact   240 tagccccctgt tgctcctcc gataactggg gtgaccttgg ttaatattca ccagcagcct   300
cccccgttgc ccctctggat ccactgctta aatacggacg aggacagggc cctgtctcct   360
cagcttcagg caccaccact gacctgggac agtgaat                            397

<210> SEQ ID NO 5
<211> LENGTH: 441
<212> TYPE: DNA
<213> ORGANISM: artificial
<220> FEATURE:
<223> OTHER INFORMATION: HBB2 intron

<400> SEQUENCE: 5
gtacacatat tgaccaaatc agggtaattt tgcatttgta attttaaaaa atgctttctt    60
cttttaatat acttttttgt ttatcttatt tctaatactt tccctaatct ctttctttca   120
gggcaataat gatacaatgt atcatgcctc tttgcaccat tctaaagaat aacagtgata   180
atttctgggt taaggcaata gcaatatttc tgcatataaa tatttctgca tataaattgt   240
aactgatgta agaggtttca tattgctaat agcagctaca atccagctac cattctgctt   300
ttattttatg gttgggataa ggctggatta ttctgagtcc aagctaggcc cttttgctaa   360
tcatgttcat acctcttatc ttcctcccac agctcctggg caacgtgctg gtctgtgtgc   420
tggcccatca ctttggcaaa g                                             441

<210> SEQ ID NO 6
<211> LENGTH: 441
<212> TYPE: DNA
<213> ORGANISM: artificial
<220> FEATURE:
<223> OTHER INFORMATION: modified HBB2 intron

<400> SEQUENCE: 6
gtacacatat tgaccaaatc agggtaattt tgcatttgta attttaaaaa atgctttctt    60
cttttaatat acttttttgt ttatcttatt tctaatactt tccctaatct ctttctttca   120
gggcaataat gatacaatgt atcatgcctc tttgcaccat tctaaagaat aacagtgata   180
atttctgggt taaggcaata gcaatatttc tgcatataaa tatttctgca tataaattgt   240
aactgatgta agaggtttca tattgctaat agcagctaca atccagctac cattctgctt   300
ttattttctg gttgggataa ggctggatta ttctgagtcc aagctaggcc cttttgctaa   360
tcttgttcat acctcttatc ttcctcccac agctcctggg caacctgctg gtctctctgc   420
tggcccatca ctttggcaaa g                                             441

<210> SEQ ID NO 7

<211> LENGTH: 1438
<212> TYPE: DNA
<213> ORGANISM: artificial
<220> FEATURE:
<223> OTHER INFORMATION: FIX intron

<400> SEQUENCE: 7

```
ggtttgtttc ctttttttaaa atacattgag tatgcttgcc ttttagatat agaaatatct      60
gatgctgtct tcttcactaa attttgatta catgatttga cagcaatatt gaagagtcta     120
acagccagca cgcaggttgg taagtactgg ttctttgtta gctaggtttt cttcttcttc     180
atttttaaaa ctaaatagat cgacaatgct tatgatgcat ttatgtttaa taaacactgt     240
tcagttcatg atttggtcat gtaattcctg ttagaaaaca ttcatctcct tggtttaaaa     300
aaattaaaag tgggaaaaca agaaatagc agaatatagt gaaaaaaaat aaccacatta      360
tttttgtttg gacttaccac tttgaaatca aatgggaaa caaaagcaca aacaatggcc      420
ttatttacac aaaaagtctg attttaagat atatgacatt tcaaggtttc agaagtatgt     480
aatgaggtgt gtctctaatt ttttaaatta tatatcttca atttaaagtt ttagttaaaa     540
cataaagatt aacctttcat tagcaagctg ttagttatca ccaacgcttt tcatggatta     600
ggaaaaaatc attttgtctc tatgtcaaac atcttggagt tgatatttgg ggaaacacaa     660
tactcagttg agttccctag gggagaaaag cacgcttaag aattgacata aagagtagga     720
agttagctaa tgcaacatat atcactttgt ttttcacaa ctacagtgac tttatgtatt      780
tcccagagga aggcatacag ggaagaaatt atcccatttg acaaacagc atgttctcac      840
aggaagcatt tatcacactt acttgtcaac tttctagaat caaatctagt agctgacagt     900
accaggatca ggggtgccaa ccctaagcac ccccagaaag ctgactggcc ctgtggttcc     960
cactccagac atgatgtcag ctgtgaaatc gacgtcgctg gaccataatt aggcttctgt    1020
tcttcaggag acatttgttc aaagtcattt gggcaaccat attctgaaaa cagcccagcc    1080
agggtgatgg atcactttgc aaagatcctc aatgagctat tttcaagtga tgacaaagtg    1140
tgaagttaac cgctcatttg agaactttct ttttcatcca agtaaattc aaatatgatt     1200
agaaatctga cctttattta ctggaattct cttgactaaa agtaaaattg aattttaatt    1260
cctaaatctc catgtgtata cagtactgtg ggaacatcac agattttggc tccatgccct    1320
aaagagaaat tggctttcag attatttgga ttaaaaacaa agactttctt aagagatgta    1380
aaattttcat gatgttttct tttttgctaa aactaaagaa ttattctttt acatttca     1438
```

<210> SEQ ID NO 8
<211> LENGTH: 1438
<212> TYPE: DNA
<213> ORGANISM: artificial
<220> FEATURE:
<223> OTHER INFORMATION: modified FIX intron

<400> SEQUENCE: 8

```
ggtttgtttc ctttttttaaa atacattgag tatgcttgcc ttttagatat agaaatatct      60
gatgctgtct tcttcactaa attttgatta catgatttga cagcaatatt gaagagtcta     120
acagccagca cgcaggttgg taagtactgg ttctttgtta gctaggtttt cttcttcttc     180
atttttaaaa ctaaatagat cgacattgct tttgttgcat ttatgtttaa taaacactgt     240
tcagttcatg atttggtcat gtaattcctg ttagaaaaca ttcatctcct tggtttaaaa     300
aaattaaaag tgggaaaaca agaaatagc agaatatagt gaaaaaaaat aaccacatta      360
tttttgtttg gacttaccac tttgaaatca aattgggaaa caaaagcaca aacaatggcc     420
```

```
ttatttacac aaaaagtctg attttaagat atatgacatt tcaaggtttc agaagtatgt       480
aatgaggtgt gtctctaatt ttttaaatta tatatcttca atttaaagtt ttagttaaaa       540
cataaagatt aacctttcat tagcaagctg ttagttatca ccaacgcttt tcatggatta       600
ggaaaaaatc attttgtctc tttgtcaaac atcttggagt tgatatttgg ggaaacacaa       660
tactcagttg agttccctag gggagaaaag cacgcttaag aattgacata aagagtagga       720
agttagctat tgcaacatat atcactttgt tttttcacaa ctacagtgac ttttgtatt        780 tcccagagga aggcatacag ggaagaaatt atcccatttg acaaacagc ttgttctcac        840 aggaagcatt tatcacactt acttgtcaac tttctagaat caaatctagt agctgacagt      900
accaggatca ggggtgccaa ccctaagcac ccccagaaag ctgactggcc ctgtggttcc      960
cactccagac atgatgtcag ctgtgaaatc gacgtcgctg gaccataatt aggcttctgt     1020
tcttcaggag acatttgttc aaagtcattt gggcaaccat attctgaaaa cagcccagcc     1080
agggtgttgg atcactttgc aaagatcctc attgagctat tttcaagtgt tgacaaagtg     1140
tgaagttaac cgctcatttg agaactttct ttttcatcca agtaaattc aaatatgatt      1200 agaaatctga cctttattta ctggaattct cttgactaaa agtaaaattg aattttaatt     1260
cctaaatctc catgtgtata cagtactgtg ggaacatcac agattttggc tccatgccct     1320
aaagagaaat tggctttcag attatttgga ttaaaaacaa agactttctt aagagatgta    1380
aaattttctt gttgttttct tttttgctaa aactaaagaa ttattctttt acatttca      1438

<210> SEQ ID NO 9
<211> LENGTH: 881
<212> TYPE: DNA
<213> ORGANISM: artificial
<220> FEATURE:
<223> OTHER INFORMATION: chicken beta-globin intron

<400> SEQUENCE: 9
gcgggagtcg ctgcgttgcc ttcgccccgt gccccgctcc gccgccgcct cgcgccgccc        60
gccccggctc tgactgaccg cgttactccc acaggtgagc gggcgggacg gcccttctcc       120
tccgggctgt aattagcgct tggtttaatg acggcttgtt tcttttctgt ggctgcgtga       180
aagccttgag gggctccggg agggcccttt gtgcgggggg agcggctcgg ggggtgcgtg       240
cgtgtgtgtg tgcgtgggga cgccgcgtg cggctccgcg ctgcccggcg ctgtgagcg        300 ctgcgggcgc ggcgcggggc tttgtgcgct ccgcagtgtg cgcgagggga gcgcggccgg       360
gggcggtgcc ccgcggtgcg ggggggctg cgagggggaac aaaggctgcg tgcggggtgt      420
gtgcgtgggg gggtgagcag ggggtgtggg cgcgtcggtc gggctgcaac ccccctgca      480 cccccctccc cgagttgctg agcacggcc ggcttcgggt gcgggctcc gtacggggcg       540 tggcgcgggg ctcgccgtgc cgggcggggg gtggcggcag gtgggggtgc cggcggggc      600 ggggccgcct cggccgggg agggctcgg ggaggggcgc ggcggccccc ggagcgccgg        660
cggctgtcga ggcgcggcga gccgcagcca ttgcctttta tggtaatcgt gcgagagggc       720
gcagggactt cctttgtccc aaatctgtgc ggagccgaaa tctgggaggc gccgccgcac       780
cccctctagc gggcgcgggg cgaagcgtg cggcgccggc aggaaggaaa tgggcgggga       840
gggccttcgt gcgtcgccgc gccgccgtcc ccttctccct c                         881

<210> SEQ ID NO 10
<211> LENGTH: 881
<212> TYPE: DNA
```

<213> ORGANISM: artificial
<220> FEATURE:
<223> OTHER INFORMATION: optimized chicken beta-globin intron

<400> SEQUENCE: 10

```
gcgggagtcg ctgcgttgcc ttcgccccgt gccccgctcc gccgccgcct cgcgccgccc    60
gccccggctc tgactgaccg cgttactccc acaggtgagc gggcgggacg gcccttctcc   120
tccgggctgt aattagcgct tggtttaatg acggcttgtt tcttttctgt ggctgcgtga   180
aagccttgag gggctccggg agggcccttt gtgcggggg agcggctcgg ggggtgcgtg    240
cgtgtgtgtg tgcgtgggga gcgccgcgtg cggctccgcg ctgcccggcg gctgtgagcg   300
ctgcgggcgc ggcgcggggc tttgtgcgct ccgcagtgtg cgcgagggga gcgcggccgg   360
gggcggtgcc ccgcggtgcg ggggggggctg cgagggggaac aaaggctgcg tgcggggtgt   420
gtgcgtgggg gggtgagcag ggggtgtggg cgcgtcggtc gggctgcaac cccccctgca   480 ccccctccc cgagttgctg agcacggccc ggcttcgggt gcggggctcc gtacggggcg    540
tggcgcgggg ctcgccgtgc cgggcggggg gtggcggcag gtgggggtgc cgggcggggc   600
ggggccgcct cgggccgggg agggctcggg ggaggggcgc ggcggccccc ggagcgccgg   660
cggctgtcga ggcgcggcga gccgcagcca ttgcctttt tggtaatcgt gcgagagggc    720
gcagggactt cctttgtccc aaatctgtgc ggagccgaaa tctgggaggc gccgccgcac   780 ccctctagc gggcgcgggg cgaagcggtg cggcgccggc aggaaggaat tgggcgggga   840
gggccttcgt gcgtcgccgc gccgccgtcc ccttctccct c                      881
```

<210> SEQ ID NO 11
<211> LENGTH: 322
<212> TYPE: DNA
<213> ORGANISM: artificial
<220> FEATURE:
<223> OTHER INFORMATION: ApoE control region

<400> SEQUENCE: 11

```
aaggctcaga ggcacacagg agtttctggg ctcaccctgc cccttccaa ccctcagtt     60 cccatcctcc agcagctgtt tgtgtgctgc ctctgaagtc cacactgaac aaacttcagc   120
ctactcatgt ccctaaaatg ggcaaacatt gcaagcagca aacagcaaac acacagccct   180
ccctgcctgc tgaccttgga gctggggcag aggtcagaga cctctctggg cccatgccac   240
ctccaacatc cactcgaccc cttggaattt cggtggagag gagcagaggt tgtcctggcg   300
tggtttaggt agtgtgagag gg                                           322
```